United States Patent
Pal et al.

(10) Patent No.: US 9,721,361 B2
(45) Date of Patent: Aug. 1, 2017

(54) SYSTEMS AND METHODS FOR PARALLEL PROCESSING OF IMAGING INFORMATION

(71) Applicants: General Electric Company, Schenectady, NY (US); The Regents of the University of Michigan, Ann Arbor, MI (US)

(72) Inventors: Debashish Pal, Waukesha, WI (US); Evgeny Drapkin, Waukesha, WI (US); Jean-Baptiste Thibault, Waukesha, WI (US); Somesh Srivastava, Waukesha, WI (US); Ryan Thome, Waukesha, WI (US); Madison G. McGaffin, Ann Arbor, MI (US); Jeffrey A. Fessler, Ann Arbor, MI (US); Donghwan Kim, Ann Arbor, MI (US)

(73) Assignees: General Electric Company, Schenectady, NY (US); The Regents of the University of Michigan, Ann Arbor, MI (US)

( * ) Notice: Subject to any disclaimer, the term of this patent is extended or adjusted under 35 U.S.C. 154(b) by 10 days.

(21) Appl. No.: 14/755,387

(22) Filed: Jun. 30, 2015

(65) Prior Publication Data

US 2016/0350944 A1    Dec. 1, 2016

Related U.S. Application Data

(60) Provisional application No. 62/168,238, filed on May 29, 2015.

(51) Int. Cl.
*G06K 9/00* (2006.01)
*G06T 11/00* (2006.01)
(Continued)

(52) U.S. Cl.
CPC .......... *G06T 11/005* (2013.01); *A61B 6/5258* (2013.01); *G06T 7/0012* (2013.01);
(Continued)

(58) Field of Classification Search
None
See application file for complete search history.

(56) References Cited

U.S. PATENT DOCUMENTS

| 9,020,230 B2 * | 4/2015 | Yu | G06T 11/006 382/131 |
| 2005/0105693 A1 * | 5/2005 | Zhao | G06T 11/006 378/210 |

(Continued)

OTHER PUBLICATIONS

Review of Parallel Computing Techniques for Computed Tomography Image Reconstruction. Ni et al. 2006.*

*Primary Examiner* — Delomia L Gilliard
(74) *Attorney, Agent, or Firm* — Dean D. Small; The Small Patent Law Group, LLC

(57) ABSTRACT

A method for iteratively reconstructing an image is provided. The method includes acquiring, with a detector, computed tomography (CT) imaging information. The method also includes generating, with at least one processor, sinogram information from the CT imaging information. Further, the method includes generating, with the at least one processor, image domain information from the CT imaging information. Also, the method includes updating the image using the sinogram information. The method further includes updating the image using the image domain information. Updating the image using the sinogram information and updating the image using the image domain information are performed separately and alternately in an iterative fashion.

20 Claims, 8 Drawing Sheets

(51) Int. Cl.
  *A61B 6/00*  (2006.01)
  *G06T 7/00*  (2017.01)
  *A61B 6/03*  (2006.01)

(52) U.S. Cl.
  CPC .............. *G06T 11/006* (2013.01); *A61B 6/032* (2013.01); *A61B 6/5205* (2013.01); *G06T 2207/10081* (2013.01); *G06T 2211/424* (2013.01)

(56) References Cited

U.S. PATENT DOCUMENTS

| | | | | |
|---|---|---|---|---|
| 2006/0072801 | A1* | 4/2006 | Bernard Deman ... | G06T 11/006 382/131 |
| 2007/0075249 | A1* | 4/2007 | Wang .................... | G06T 11/006 250/363.04 |
| 2011/0262054 | A1* | 10/2011 | Benson ................ | G01N 23/046 382/275 |
| 2012/0155728 | A1* | 6/2012 | DeMan ................. | G06T 11/006 382/131 |
| 2013/0343673 | A1* | 12/2013 | Pal ........................ | G06T 11/003 382/298 |
| 2016/0055658 | A1* | 2/2016 | Liang ................... | G06T 11/006 382/131 |

* cited by examiner

1: Initialize $\tilde{x}^{(0)}$ by FBP, and compute $D$.
2: Distribute image $\tilde{x}^{(0)}$ and data $y$ into $B$ nodes.
3: for $n = 0, 1, \ldots$
4:   Minimize $\phi_{BSS}(x;\tilde{x}^{(n)})$ in (8)
         using $L$ sub-iterations of OS-SQS-mom.
   1) Initialize $x^{(0)} = z^{(0)}$ by $\tilde{x}^{(n)}$, and $t^{(0)} = 1$.
   2) for $l = 0, 1, \ldots, L - 1$
   3)   $m = l \bmod M$
   4)   $t^{(l+1)} = \frac{1}{2}\left(1 + \sqrt{1 + 4[t^{(l)}]^2}\right)$
   5)   for $b = 1, \ldots, B$ simultaneously
   6)     $g_{m,b}^{(l)} = M\nabla_b \psi_{BSS}(z^{(\frac{l}{M})}, z^{(0)})$
   7)     $x_b^{(\frac{l+1}{M})} = \left[z_b^{(\frac{l}{M})} - D_b^{-1} g_{m,b}^{(l)}\right]$
   8)     $z_b^{(\frac{l+1}{M})} = x_b^{(\frac{l+1}{M})} + \frac{t^{(l)} - 1}{t^{(l+1)}}\left(x_b^{(\frac{l+1}{M})} - x_b^{(\frac{l}{M})}\right)$
   9)   end for
   10) end for
   11) $\tilde{x}^{(n+1)} = x^{(\frac{L}{M})}$
5:   Communicate $\tilde{x}^{(n+1)}$.
6: end for

FIG. 5

SYSTEMS AND METHODS FOR PARALLEL PROCESSING OF IMAGING INFORMATION

RELATED APPLICATIONS

The present application makes reference to and claims priority to U.S. Provisional Application No. 62/168,238, filed May 29, 2015, entitled "Systems and Methods for Parallel Processing of Imaging Information," the entire subject matter of which is incorporated by reference herein.

STATEMENT OF GOVERNMENT RIGHTS

This invention was made with government support under Contract NIH Grant EB018753. The government has certain rights in the invention.

BACKGROUND OF THE INVENTION

The subject matter disclosed herein relates generally to systems and methods for computed tomography (CT) imaging, for example to systems and methods for using model based image reconstruction (MBIR) or other iterative approaches to reconstruction a CT image.

In CT imaging, an X-ray source may be rotated around an object to obtain imaging information. X-rays from the source attenuated by the object may be collected or detected by a detector and used to reconstruct an image.

Statistical and/or model based X-ray CT reconstruction may reduce noise and artifacts using safer low-dose CT scans compared to conventional filtered back-projection (FBP) methods; however, certain previous approaches utilizing such reconstruction (e.g., of large helical CT scan data) techniques require overly long computation times. For example, even if aspects of previous approaches could be performed in parallel, significant time may be consumed due to periods of time during which one or more processors remain idle time while waiting on data transfer.

BRIEF DESCRIPTION OF THE INVENTION

In one embodiment, a method for iteratively reconstructing an image is provided. The method includes acquiring, with a detector, computed tomography (CT) imaging information. The method also includes generating, with at least one processor, sinogram information from the CT imaging information. Further, the method includes generating, with the at least one processor, image domain information from the CT imaging information. Also, the method includes updating the image using the sinogram information. The method further includes updating the image using the image domain information. Updating the image using the sinogram information and updating the image using the image domain information are performed separately and alternately in an iterative fashion.

In another embodiment, a reconstruction system is provided that includes a central processor and plural distributed processors. The distributed processors are configured to perform parallel processing under the direction of the central processor. The reconstruction system is configured to acquire CT imaging information, determine block-separable surrogates for analyzing the CT imaging information, assign each block-separable surrogate component to a corresponding distributed processor, with the corresponding distributed processor configured to minimize a component of the block-separable surrogate, perform multiple iterations of an algorithm to minimize the block-separable surrogates independently using the corresponding distributed processors, and synchronize the block-separable surrogates after performing the multiple iterations using the corresponding distributed processors.

In another embodiment, a reconstruction system is provided that includes a central processor and one or more distributed processors. The distributed processors are configured to perform parallel processing under the direction of the central processor. The reconstruction system is configured to perform an operation utilizing resident information initially resident upon one of the distributed processors and non-resident information transferred from at least one other of the distributed processors. The one of the distributed processors (e.g., the processor upon which the resident information is initially resident) is configured to begin performing the operation using the resident information, receive the non-resident information during at least a portion of a time utilized to begin performing the operation using the resident information, and complete performing the operation using the non-resident information.

BRIEF DESCRIPTION OF THE DRAWINGS

FIG. 5 summarizes an example distributed BSS algorithm that guarantees monotonic descent update and convergence for the one-subset (M=1) version.

DETAILED DESCRIPTION OF THE INVENTION

Figure 1:
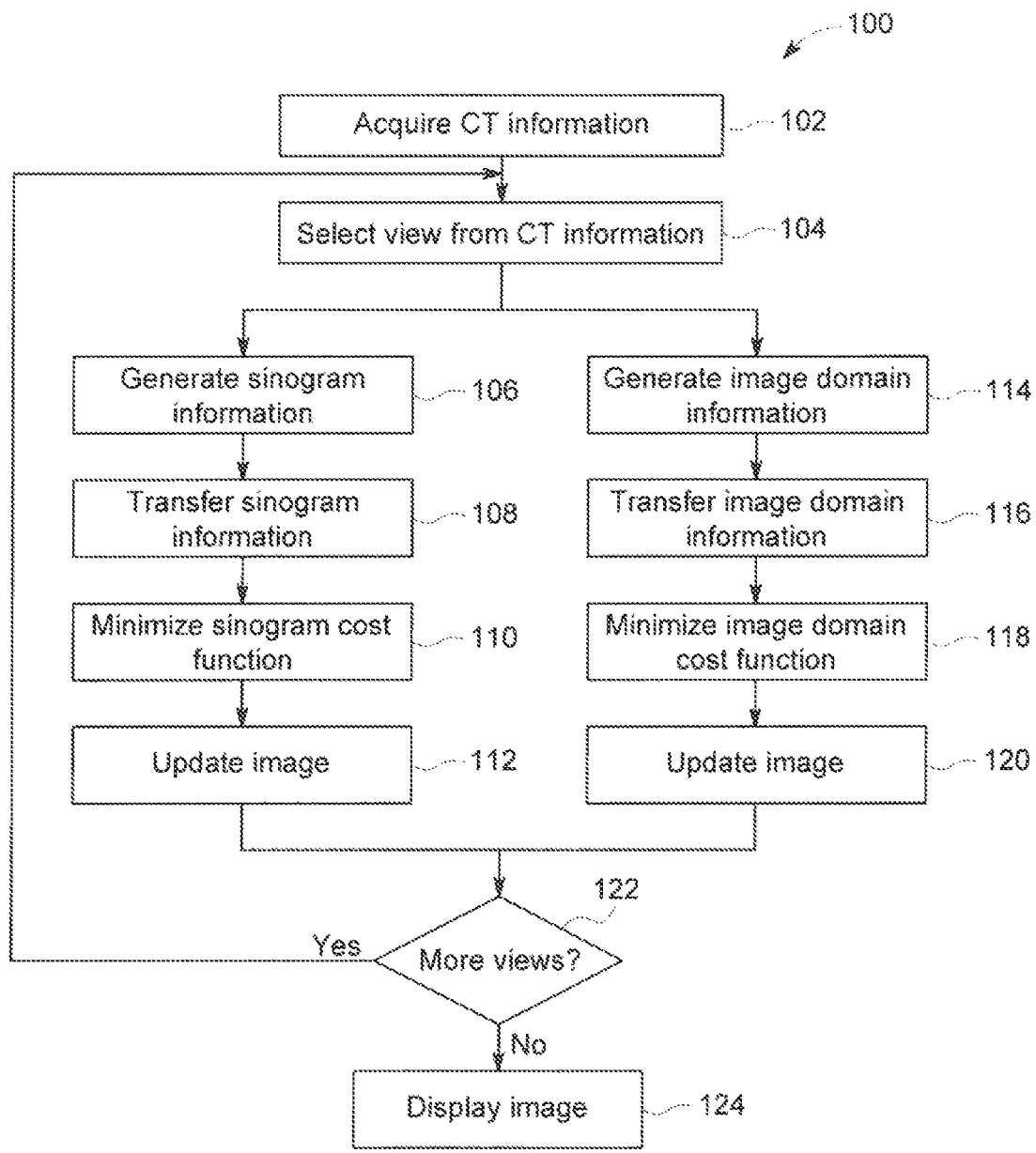
FIG. 1 is a flowchart of a method in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should be further understood that the figures illustrate example embodiments of the present disclosure. Variations, such as replacing or modifying one or more functional blocks, are possible to achieve similar results.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also used herein, the phrase "reconstructing an image" is not intended to exclude embodiments in which data representing an image is generated, but a viewable image is not. As used herein, the term "image" broadly refers to both viewable images and data representing a viewable image. It may be noted that various embodiments generate, or are configured to generate, at least one viewable image.

Various embodiments provide systems and methods for improved efficiency parallel processing of imaging information, for example to reconstruct an image using an iterative and/or model-based technique. For example, model-based image reconstruction (MBIR) for CT may have large computational requirements and require many computational elements or cores to achieve practical reconstruction times.

In various embodiments, algorithms tailored to parallel computing may be employed. For example, such algorithms may be employed with computing or processing nodes that use distributed processors or external co-processors (e.g., GPUs) that are not connected directly to RAM of a main or central host and thus require explicit memory transfers between the host and the co-processors. While such systems may provide numerous computing cores, data communication may become a major bottleneck in such system. Various embodiments disclosed herein improve efficiency of such systems, for example by using duality (and/or other techniques) to separate at least a portion of the updates related to sinogram data from updates related to image domain data (e.g., regularizer data) such that computation of the updates may be interleaved efficiently with data transfer (e.g., one type of information transferred while an update using a different type of information is performed).

In various embodiments, MBIR (or other reconstruction technique) may be implemented on a single or multiple compute devices using a combination of system and/or algorithmic techniques. For example, an iterative technique for CT reconstruction may be employed that alternates between updating an image using portions of sinogram data (e.g., a view at a time) and updating variables related to the regularizer. During each update, data may be transferred to the computational device for subsequent updates. The regularizer and image updates may be designed using duality such that the algorithm is guaranteed to converge. In some embodiments, the sinogram views may be chosen randomly or pseudo-randomly. The dual variables may be associated with sinogram elements and with differences between neighboring voxels for the regularizer (or other relationships between neighboring pixels). In some embodiments, the image volume data may be partitioned across multiple compute devices (e.g., GPUs) in a fashion favorable to computation by rows, columns, or slices of the image volume. Further still, the image volume data may be pro-integrated across one or two dimensions to improve computation performance of a forward-projection algorithm and/or a back-projection algorithm on a highly parallel computing architecture.

Additionally or alternatively, various embodiments allow different nodes of a system to perform multiple image updates (and/or other iterative processes) between data communication phases. For example, in some embodiments, a block separable surrogate function method has been adapted to CT reconstruction. For example, an image data volume may be partitioned into disjoint axial-slabs. Slices on the slab boundary may converge more slowly (in iterations) due to BSS, but multiple numbers of iterations may be performed before synchronization, thereby reducing communication time. To help make the convergence rate more uniform, the partition boundary may be dithered between updates to vary which slices are on the boundary.

Further additionally or alternatively, in various embodiments, an algorithm (e.g., a simultaneous MBIR algorithm) may be implemented on multiple compute devices (or nodes). The latency of communicating between the multiple compute devices (e.g., CPU) may be "hidden" behind concurrent calculations. In various embodiments, some portion of image volume data starts resident on a compute device or node (e.g., GPU) to be used for calculations of a next subset and/or iteration, thereby enabling additional image volume data for subsequent computations to be transferred simultaneously or concurrently with computations using data already resident on the node without performance penalty (or with minimized or reduced performance penalty). Alternatively or additionally, some portion of sinogram data starts resident on a compute device or node (e.g., GPU) to be used for calculations of a next subset and/or iteration, thereby enabling additional sinogram data for subsequent computations to be transferred simultaneously or concurrently with computations using data already resident on the node without performance penalty (or with minimized or reduced performance penalty).

Various embodiments provide improved imaging. A technical effect of at least one embodiment includes reducing compute time required to reconstruct an image, for example using model-based or other iterative techniques. A technical effect of at least one embodiment includes reduction of radiation dose. A technical effect of at least one embodiment includes improved image quality.

FIG. 1 provides a flowchart of a method 100 for reconstructing an image of an object, for example model based iterative reconstruction (MBIR), in accordance with various embodiments. The method 100, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 100 may be able to be used as one or more algorithms to direct hardware (e.g., one or more aspects of the processing unit 200 and/or image reconstructor 950) to perform one or more operations described herein. It may be noted that, in the illustrated embodiment, an MBIR or other iterative cost minimization technique is employed. In other embodiments, other techniques may be employed additionally or alternatively.

At 102, CT information is acquired. The CT information may be collected by rotating an X-ray source and detector relative to an object to be imaged. In some embodiments, the CT information may also be collected by translating the X-ray source and detector axially or longitudinally relative to the object to be imaged. The axial or longitudinal translation may occur at the same time as the rotation in some embodiments (e.g., during a helical mode of operation), or may occur in steps or increments between rotations (e.g., during a step and shoot mode of operation). It may be noted that in some embodiments, the CT imaging information may be acquired from a storage device, memory device, and/or network or internet connection. The processors that acquire the CT imaging information for use in reconstruction may be integral with an acquisition unit as part of an imaging system located at a single location, or the processors may be located remotely from the acquisition unit.

After the CT information is acquired, the collected CT information may be used to reconstruct an image. In the illustrated embodiment, an iterative reconstruction process is employed. Both sinogram information (e.g., information from a sinogram domain representation of the CT information) and image domain information (e.g., regularizer information) are employed in updating an image as part of an iterative reconstruction process in the illustrated embodiment. In contrast to certain conventional approaches, however, updates using the sinogram information and updates using the image domain information are separately applied. Accordingly, systems and methods utilizing the method 100 may be utilized more efficiently than conventional approaches. For example, while data relating to one of the sinogram information or the image domain information is being transferred, data relating to the other of the sinogram information or the image domain information may be used to update the image, reducing time spent idly waiting for completion of data transfer and increasing processing efficiency. In various embodiments, as discussed herein, the processing may be performed using distributed processors operating in parallel.

At 104, a view is selected from the CT information. The CT information may be acquired as a series of views, with each view corresponding to a given projection angle or rotational position of the X-ray source with respect to the object being imaged. In the illustrated embodiment, the image is updated using information from one view at a time. The sequence of views may be selected randomly. Use of randomly selected views may help reduce or minimize overlap between adjacent views in the sequence of views used to update. Other techniques, such as selecting the views in bit-reversed order, may be utilized in some embodiments to select the particular sequence in which the views are employed to update the image. It may be noted that in the illustrated embodiment, the method is performed view by view (e.g., sinogram information for one view used to update, then image domain information used to update the image, then sinogram information for a next view used to update, then image domain information used to update the image); however, other sequences (e.g., groups of views for sinogram information used to update the image followed by groups of views of image domain information used to update the image) may be employed in alternate embodiments. Portions of a view or views could be used for an update in another embodiment, rather than entire views.

At 106, sinogram information (or tomography information) is generated from the CT information. For example, the sinogram information may be selected from the CT information for a particular selected view. At least some of the sinogram information may be transformed from a sinogram domain to an imaging domain, for example to update an image. At various stages of processing, the sinogram information may be back projected to provide tomography information in an image domain, or tomography information may be forward projected from an image domain to a sinogram domain.

At 108 in the depicted embodiment, sinogram information is transferred from a central processing unit (CPU) to a distributed processing unit. The distributed processing unit, for example, may be a graphics processing unit (GPU). The sinogram information may be transferred to more than one distributed processing unit in various embodiments. However, in some embodiments, the processing may be performed with a single processing node, or without the use of distributed processing nodes (e.g., GPU or other distributed processors).

Figure 2:
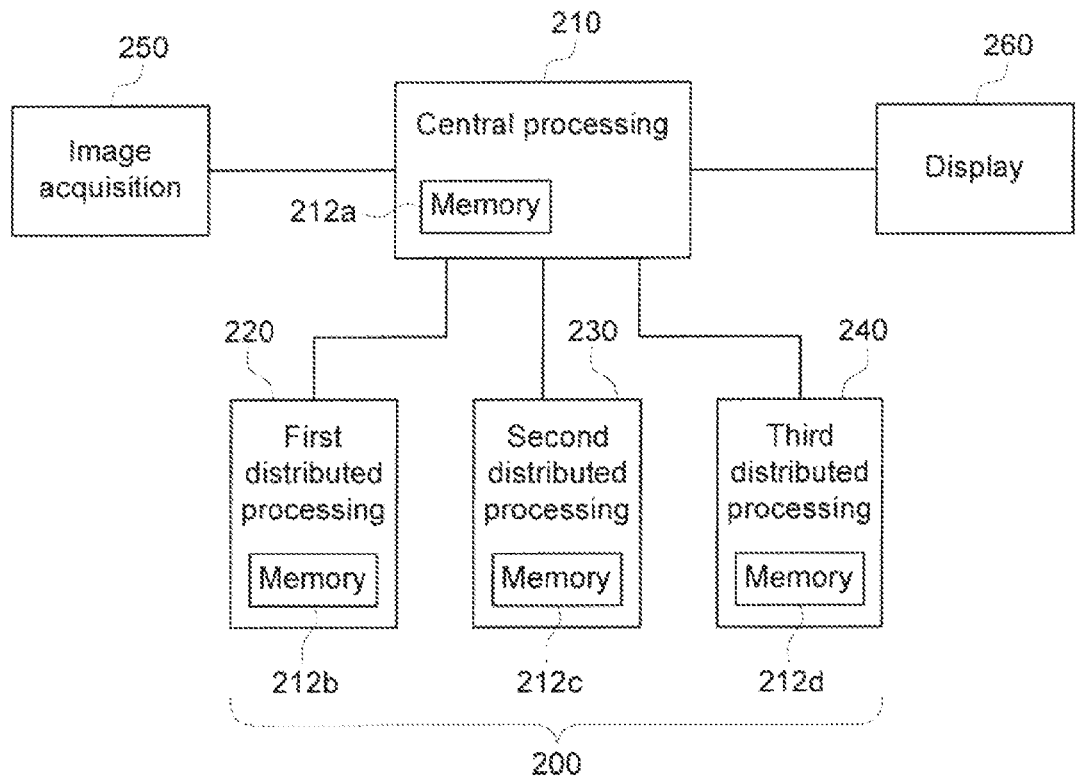
FIG. 2 is a schematic block diagram illustrating an image reconstruction system in accordance with various embodiments.

FIG. 2 is a schematic block diagram illustrating an image reconstruction system 200 that includes distributed processing units in accordance with various embodiments. The image reconstruction system 200 may be operably coupled to an image acquisition unit 250, and a display unit 260. Generally, the image reconstruction system acquires CT imaging information via the acquisition unit, generates a reconstructed image (e.g., using MBIR or other iterative technique), and provides a reconstructed image to the display unit 260 for display and/or storage for later display. The image reconstruction system 200 may be configured to utilize one or more portions of the methods or processes discussed herein to reconstruct an image.

As seen in FIG. 2, the image reconstruction system includes a central processing unit 210, a first distributed processing unit 220, a second distributed processing unit 230, and a third distributed processing unit 240. Generally, the distributed processing units 220, 230, 240 are connected in parallel with the central processing unit 210. Processing units, for example, may also be referred to as nodes. Each of the distributed processing units 220, 230, 240 may be configured to perform operations, such as minimization of a cost function or other operation as part of an iterative image reconstruction process. As depicted in FIG. 2, each of the processing units includes a memory 212 (e.g., 212a, 212b, 212c, 212d). The memory 212 may include one or more computer readable storage media. The memory 212 of each of the processing units, for example, may store imaging information, results of intermediate processing steps, or the like. Further, the process flows and/or flowcharts discussed herein (or aspects thereof) may represent one or more sets of instructions that are stored in one or more of the memories 212 for direction of operations of the system 200. It may be noted that the various nodes or processors depicted in FIG. 2 do not share memory. The various depicted processing units may include processing circuitry configured to perform one or more tasks, functions, or steps discussed herein. It may be noted that operations performed by the processing units (e.g., operations corresponding to process flows or methods discussed herein, or aspects thereof) may be sufficiently complex that the operations may not be performed by a human being within a reasonable time period.

The central processing unit 210 may receive the CT imaging information from the image acquisition unit 250, separate the CT imaging information (e.g., into tomography information and image domain information on a view-by-view basis) and distribute the separated portions of the CT imaging information among the distributed processing units 220, 230, 240.

Accordingly, one aspect of processing (e.g., performing an update using tomography information) may be performed by one of the distributed processing units while information for a different aspect of processing (e.g., information for use in performing an update using image domain information such as regularizer information) is being transferred to or from a different one of the distributed processing units. It may be noted that a given distributed processing unit may be configured only for use with a given type of information (e.g., dedicated to processing sinogram information but not image domain information, dedicated to processing image domain information but not sinogram information). Alternatively, a given distributed processing unit may be configured for processing sinogram information as well as image domain information at different times. Further, one or more of the distributed processing units may be configured for projecting or transforming information between sinogram and image domains. In some embodiments, one or more distributed processing units may determine an update to be performed on an image, while the central processing unit 210 applies the updates.

Returning to FIG. 1, at 110, a sinogram cost function is minimized using the sinogram information to produce optimized sinogram information, for example in connection with MBIR. The cost function may be minimized using a convex conjugate as discussed elsewhere herein in further detail. At 112, the image is updated using the optimized sinogram information. It may be noted that other techniques alternatively or additionally to MBIR may be utilized to produce the sinogram or tomography information used to update the image at 112. Further, the sinogram or tomography information may be transformed from a sinogram domain to an image domain before using the sinogram information to update the image. Further still, it may be noted that an initial image (e.g., an image to which the first update in an iterative process is applied) may be generated using a fast filtered backprojection method as known in the art.

In various embodiments, during the transfer and/or processing and/or updating related to the sinogram or tomography information, one or more steps regarding image domain information may be performed separately from the steps regarding sinogram or tomography information. In the illustrated embodiment, at 114, image domain information is generated from the CT information. For example, the image domain information may be generated using an initial image for a first iteration, or using a previously updated image (e.g., an image updated based on a previous view of sinogram information). In various embodiments, the image domain information may include regularizer information. Generally, as used herein, regularizer information may be understood as information corresponding to relationships of pixels in an image. For example, relationships between all or some of a group of pixels within a predetermined range may be utilized to generate the regularizer information. In some embodiments the pixels may be neighboring or near to each other. For example, in some embodiments, the regularizer information may include differences between immediately adjacent pixels. Again, it may be noted that different relationships other than a difference and/or different groups of neighboring pixels alternatively or additionally to immediately adjacent pixels may be employed. Further still, it may be noted that neighboring pixels of a given pixel may be separated into different groups and processed separately (e.g., by different distributed processing units). For example, for a single voxel in a 3-D array, the given voxel will have 26 different immediately adjacent neighbors (e.g., voxels having at least an edge or point of an edge in common with the given voxel). In various embodiments, the 26 neighbors may be separated into two or more groups, and corresponding regularizer information may be developed and/or processed separately for the groups. It may be noted that other forms of image domain information, for example non-negativity information, may be utilized additionally or alternatively to regularizer information.

At 116 in the depicted embodiment, image domain information is transferred from a central processing unit (CPU) to a distributed processing unit. The image domain information may be transferred from a distributed processing unit to a different distributed processing unit via the CPU. The distributed processing unit, for example, may be a graphics processing unit (GPU). It may be noted that the image domain information may be transferred to more than one distributed processing unit in various embodiments (e.g., different portions of regularizer information transferred to different distributed processing units, regularizer information transferred to a given distributed processing unit (or units) and non-negativity information transferred to a different distributed processing unit (or units), among others). However, in some embodiments, the processing may be performed with a single processing node, or without the use of distributed processing nodes (e.g., GPU or other distributed processors).

At 118, an image domain cost function (e.g., a regularizer function) is minimized using the image domain information to produce optimized image domain information, for example in connection with MBIR. The cost function may be minimized using a convex conjugate as discussed elsewhere herein in further detail. At 120, the image is updated using the optimized image domain information. It may be noted that other techniques alternatively or additionally to MBIR may be utilized to produce the image domain information used to update the image at 120.

In the illustrated embodiment, the updating of the image using image domain information (e.g., at 120) and the updating of the image using sinogram or tomography information (e.g., at 112) are performed separately and alternately in an iterative fashion. For example, a tomography information-based update may be performed for a selected view, followed by a separate image domain information-based updated (e.g., regularizer-based update) for the selected view.

With reference to FIG. 2, it may be noted that in various embodiments, the distributed processing units 220, 230, 240 are configured to perform parallel processing under the direction of the central processing unit 210. Accordingly, one of the of the distributed processing units (e.g., first distributed processing unit 220) may be employed to perform minimization of the sinogram information cost function (and/or other processing related to the sinogram information), while a different one of the distributed processing units (e.g., second distributed processing unit 230 and/or third distributed processing unit 240) is employed to perform minimization of the image domain information cost function (and/or other processing related to the image domain information).

The transfer of one type of information may be performed while processing is performed on a different type of information, thereby improving processor efficiency by reducing idle time waiting for transfer of both types of information before processing. For example, at least some of the sinogram or tomography information may be transferred from the central processing unit 210 to at least one of the distributed processing units (e.g., first distributed processing unit 220) while a different one of the distributed processing units (e.g., second distributed processing unit 230) is performing the minimization of the image domain cost function (or other operation using the image domain information). Similarly, at least some of the image domain information may be transferred from the central processing unit 210 to at least one of the distributed processing units (e.g., second distributed processing unit 230) while a different one of the distributed processing units (e.g., first distributed processing unit 220) is performing the minimization of the sinogram cost function (or other operation using the sinogram information).

It may be noted that additional techniques may be employed additionally or alternatively to improve processor efficiency. For example, the distributed processing units may transfer or share with each other, for example, via the central processing unit 210. In some embodiments, a distributed processing unit (e.g., first distributed processing unit 220) may utilize both resident information (or information previously generated by the first distributed processing unit 220) and non-resident information (e.g., information generated by other processing units) to perform a given operation. The first distributed processing unit 220 may begin performing the operation using the resident information while receiving non-resident information from one or both of the second distributed processing unit 230 and third distributed processing unit 240. The first distributed processing unit 220 may complete performing the operation using the non-resident information after the non-resident information has been received. Accordingly, processing efficiency may be improved, for example, by beginning a processing step with a portion of information that is readily available while receiving a portion from one or more other processing units. Additional discussion regarding beginning performing of an operation while receiving information for performing the operation (or receiving information on a just-in-time basis) may be found herein at FIGS. 6 and 7 and the related discussion.

Additionally or alternatively, the central processing unit 210 may be configured to distribute at least one of the sinogram information or the image domain information using block-separable surrogate functions. For example, the first distributed processing unit 220 may perform multiple iterations of a first block-separable surrogate function while the second distributed processing unit 230 performs multiple iterations of a second block-separable surrogate function. Additional discussion regarding block-separable surrogates may be found herein at FIGS. 4 and 5 and the related discussion.

Returning to FIG. 1, at 122, it is determined if more views of the CT information are to be used to reconstruct the image. If one or more additional views are to be used, the method proceeds to 104, where a new view is selected to be used as a new current view. If no more views are to be utilized, the method proceeds to 124. At 124, the image is displayed, for example, on a screen or printout. Additionally or alternatively, the image may be stored for further processing and/or display at a later time. It may be noted that processing and/or transfer of information for different views of the CT information may occur simultaneously or concurrently. For example, while an image domain update for a previous view is being determined and/or applied, sinogram or tomography information for a subsequent view may begin the transfer and/or processing steps using a different distributed processor than is being used for image domain update.

Accordingly, for example using one or more aspects of the method 100, processing efficiency for an iterative reconstructive process may be improved. Certain general considerations as well as particular examples of aspects of iterative reconstructive processes that may be used in conjunction with one or more aspects of the method 100 will now be discussed. Generally, MBIR methods for X-ray reconstruction may improve image quality and reduce patient X-ray dose. MBIR methods produce images by solving high-dimensional, statistically motivated numerical optimization problems. Unfortunately, MBIR methods may require relatively high computation costs to solve the optimization problems. However, by improving processing or computational efficiency using one or more techniques as discussed herein, MBIR (or other iterative reconstruction techniques) may be more practically achieved. Various embodiments discussed herein may use duality and/or group coordinate ascent to alternately perform efficient tomography and de-noising (and/or other image domain information-based) updates. Various embodiments may employ non-smooth regularizers such as total variation (TV), and may store only two image-sized vectors on a GPU (or other distributed processing unit).

For example, consider the following model-based X-ray image reconstruction (MBIR) problem:

$$\hat{x} = \operatorname*{argmin}_{x} L(Ax) + R(Cx) \qquad \text{Eq. 1}$$

With X-ray CT system matrix A, 3D finite differencing matrix C, log-likelihood data-fit term L, and edge-preserving regularizer R. It may be noted that examples discussed herein may not include a non-negativity constraint; however in various embodiments the techniques discussed herein may be extended to accommodate a non-negativity constraint. Both L and R are separable sums of convex functions:

$$L(Ax) = \sum_{i=1}^{M} l_i([Ax]_i) \quad R(Cx) = \sum_{k=1}^{N_d} r_k([Cx]_k). \qquad \text{Eq 2:}$$

Accordingly, L and R may be separated or de-coupled, and addressed separately. One possible choice for the data-fit term L is the Gaussian-inspired quadratic term $$L(Ax) = \frac{1}{2}\|Ax - y\|_W^2$$

with noisy measurements y and diagonal matrix of positive statistical weights W. The edge-preserving regularizer may be a weighted sum of nonquadratically penalized finite differences, $$r_k = \beta_k \psi([Cx]_k) = \beta_k \psi(x_{k1} - x_{k2}) \quad \text{Eq 3:}$$

with convex $\psi$ and $\beta_k > 0$. This includes anisotropic total variation (TV) and many other noise-reducing regularizers. In Eq. 3, the $(x_{k1} - x_{k2})$ term corresponds to differences between two (in some embodiments, two neighboring) pixel values.

An image produced by solving Eq. 1 may be higher quality than images produced with conventional filtered-backprojection methods, and MBIR algorithms may produce diagnostically useful images at lower doses than conventional CT reconstruction algorithms. Unfortunately, solving MBIR's optimization problem may be computationally challenging and time-consuming in comparison with conventional methods. However, as disclosed herein, use of algorithms in connection with highly parallel hardware improves computational and processing efficiency and makes MBIR's advantages more practically attainable. Various embodiments utilize techniques that combine the high parallelism available in modern GPUs with structure-exploiting algorithms to solve MBIR optimization problems.

First a framework for certain algorithms will be discussed. Let $x^{(n)} \in \mathbb{R}^{(N)}$ be an estimate of $\hat{x}$. Customarily, $x^{(0)}$, the initial image, is generated using a fast filtered backprojection method. An example algorithm discussed herein has two steps that are alternated between until convergence. First, identify an update $d^{(n)}$ to $x^{(n)}$, and then apply the update, generating $x^{(n+1)} = x^{(n)} + d^{(n)}$. The first step may be performed by approximately solving the following optimization problem:

$$d^{(n)} = \underset{d}{\operatorname{argmin}} L(Ax^n = Ad) + R(Cx^{(n)} + Cd) + \frac{\epsilon}{2}\|d\|_2^2 \quad \text{Eq. 4}$$

with $\epsilon > 0$. It may be noted that solving Eq. 4 may be nearly as challenging as solving the original optimization problem given by Eq. 1; however the final term of Eq. 4 allows use of a duality approach.

In one example duality approach utilized in some embodiments, L* and R* are convex conjugates of L and R, respectively:

$$L^*(u) = \sum_{i=1}^{M} l_i^*(u_i), \quad R^*(v) = \sum_{k=1}^{N_d} r_k^*(v_k). \quad \text{Eq. 5}$$

Where $l_i^*$ and $r_k^*$ are the convex conjugates of $l_i$ and $r_k$, respectively. Eq. 4 may be rewritten using the biconjugate property of the convex functions L and R:

$$d^{(n)} + \underset{d}{\operatorname{argmin}} \underset{u,v}{\operatorname{max}} u^T A(x^{(n)} + d) + \quad \text{Eq. 6}$$
$$v^T C(x^{(n)} + d) - L^*(u) - R^*(v) + + \frac{\epsilon}{2}\|d\|_2^2$$

After swapping the order of the "min" and "max" in Eq. 6, the update d(n) may be solved for in terms of u and v:

$$d^{(n)}(u, v) = -\frac{1}{\epsilon}(A^T u + C^T v) \quad \text{Eq. 7}$$

Plugging Eq. 7 back into Eq. 6 produces the dual problem:

$$u^{(n)}, v^{(n)} = \underset{u,v}{\operatorname{argmax}} D^{(n)}(u, v), \text{ where} \quad \text{Eq. 8}$$

$$D^{(n)}(u, v) \triangleq -L^*(u) - R^*(v) + u^T A x^{(n)} + v^T C x^{(n)} - \frac{1}{2}\|A^T u + C^T v\|_2^2 \quad \text{Eq. 9}$$

Eq. 8 may be approximately solved with a coordinate ascent method that is similar to stochastic dual coordinate ascent (SDCA). In various embodiments, in each of $N_{inner}$ inner iterations, a group of elements of either u or v may be randomly chosen, and, holding all other variables constant, the selected group of variables may be updated to increase the dual function $D^{(n)}(u,v)$. This inner procedure is a relatively simple, convergent group coordinate ascent algorithm. As used herein, optimizations over elements of u may be referred to as sinogram updates or tomography updates, and optimizations over elements of v may be referred to as image domain information updates, such as regularizer updates (e.g., denoising updates).

With respect to tomography updates, a duality-based proximal technique may efficiently solve quadratic problems involving the CT system matrix A. Unlike ordered subsets (OS) approximations, the duality-based approach is convergent.

In an example duality-based approach, one view of u at a time, written $u_\beta$, may updated. The corresponding CT projection operator, noisy data, and statistical weights are $A_\beta$, $y_\beta$, and $W_\beta$, respectively. Tomography terms unrelated to $u_\beta$ are indicated using the subscript "\β" (e.g., $u_{\backslash\beta}$). Holding all variables other than up constant, it is desired to find $u_\beta^+$ such that:

$$D^{(n)}(u_\beta^+, u_{\backslash\beta}, v) \geq D^{(n)}(u_\beta^+, u_{\backslash\beta}, v) \quad \text{Eq. 10:}$$

and then update $u_\beta \leftarrow u_\beta^+$ in place. $u_\beta^+$ may be found as the maximizer of the minorizing surrogate function $S_\beta$ for $D^{(n)}$:

$$u_\beta^+ = \underset{u_\beta}{\operatorname{argmax}} S_\beta(u_\beta; u, v, x^{(n)}), \text{ where,} \quad \text{Eq. 11}$$

$$S_\beta(u_\beta^+; u, v, x^{(n)}) = \quad \text{Eq. 12}$$
$$-L_\beta^*(u_\beta^+) - \frac{1}{2}\|u_\beta^+ - u_\beta\|_{M_\beta}^2 + (u_\beta^+)^T A_\beta(x^{(n)} + d^{(n)}(u, v))$$

Updating $u_\beta^+$ in this way will increase the dual function D(n) if $M_\beta \geq A_\beta A_\beta^T$, i.e., if all the eigenvalues of $M_\beta - A_\beta A_\beta^T$ are non-negative. Finding the "tightest" so-called majorizer for $A_\beta A_\beta^T$ may be challenging; however, the following diagonal matrix is relatively easy to compute and useful in practice:

$$M_\beta = \underset{t}{\operatorname{diag}}\{[A_\beta A_\beta^T 1]_i\} \quad \text{Eq. 13}$$

These $M_\beta$ depend only on A (i.e., they are independent of any patient data) so they may be precomputed. It may be noted that storing Mb for all β may utilize the same amount of memory as the projection data y.

When $L(Ax) = \frac{1}{2}\|Ax - y\|_W^2$, the update (11) is $$u_\beta^+ \leftarrow u_\beta + \epsilon W_\beta (\epsilon I + W_\beta W_\beta)^{-1}$$
$$(A_\beta(x^{(n)} + d^{(n)}(u, v)) - y_\beta - u_\beta)$$

Eq. 14

It may be noted that the major computational costs of implementing Equation 14 are the one-view forward projection ($A_\beta$), a series of diagonal operations, and a one-view backprojection to update $d^{(n)}(u,v)$.

With respect to do-noising updates, one example regularizer R utilized in various embodiments couples neighboring pixels together through a finite differencing matrix C. This property may be utilized to update groups of pixels from different neighborhoods simultaneously, providing a fast de-noising algorithm. The dual function D(n) has a similar structure as a function of v. For example, let D be the number of directions along which R penalizes voxel differences (e.g., horizontal, vertical, axial, etc.), with $v = [v_1^T \ldots v_D^T]^T$. Because R* is separable, the only coupling between different elements of v comes from the quadratic term:

$$\|A^T u + C^T v\|^2 = \begin{bmatrix} v_1 \\ \vdots \\ v_D \end{bmatrix}^T \begin{bmatrix} C_1 C_1^T & \cdots & C_1 C_D^T \\ \vdots & \ddots & \vdots \\ C_D C_1^T & \cdots & C_D C_D^T \end{bmatrix} \begin{bmatrix} v_1 \\ \vdots \\ v_D \end{bmatrix} + 2v^T CA^T u + c(u),$$

Eq. 15 where each $C_d$ is a banded upper triangular finite differencing matrix in a single direction with 1s along the diagonal and −1s along an upper band.

To optimize over one "direction" of differences at a time, all variables except one $v_d$ may be held constant. The entries of $v_d$ are coupled in the dual function by $C_d C_d^T$. It may be noted that only differences that are adjacent to one another along the $d^{th}$ direction are coupled by $C_d C_d^T$. For example, if d corresponds to the horizontal direction, then the only elements of $v_d$ coupled by $C_d C_d^T$ are those horizontally adjacent to one another. If optimization is first performed over the "even" entries of $v_d$, and then optimization is performed over the "odd" entries of $v_d$, each of these half-$v_d$ optimizations will be over decoupled variables. Consequently, they may be performed independently and in parallel (e.g., utilizing different distributed processing units).

For example, let $v_g$ be one such half-$v_d$ group and $C_g$ be the matrix of corresponding rows from $C_d$. The updated $v_g^+$ may found by maximizing the following separable surrogate for D(n):

$$v_g^+ = \underset{v_g}{\operatorname{argmax}} S_g(v_g; u, v, x^{(n)}),$$

Eq. 16

$$S_g(v_g^+; u, v, x^{(n)}) = \sum_{v_k^+ \in v_g} s_k(v_g^+; u, v, x^{(n)}),$$

Eq. 17

$$s_k(v_g^+; u, v, x^{(n)}) =$$

$$v_k^+ [C_g(x^{(n)} + d^{(n)}(u, v))]_k - r_k^*(v_k^+) - \frac{1}{2\epsilon}\|C_g e_k\|^2 (v_k^+ - v_k)^2$$

Eq. 18 where $e_k$ is the $k^{th}$ elementary basis vector.

If the dual function $r_k^*$ has a convenient closed form, then the elements of $v_g^+$ may be computed from Eq. 18. While this is true for the absolute value and quadratic potential functions, this may not always be the case. Instead, if the potential function ψ has a closed form shrinkage function, Eq. 18 may be maximized by again invoking duality.

$$v_k^+ = v_k + \frac{\epsilon}{2}(q_k - z_k),$$

Eq. 19

$$q_k = [C_g(x^{(n)} + d^{(n)}(u, v))]_k,$$

Eq. 20

$$z_k = \underset{z}{\operatorname{argmin}} \frac{\epsilon}{4}\left(z - \left(q_k + \frac{2}{\epsilon}v_k\right)\right)^2 + r_k(z)$$

Eq. 21

This approach is more convenient for the many potential functions with closed-form shrinkage operators but complicated dual functions, such as the Fair potential.

Next, certain aspects of implementation of the algorithms discussed above on one or more GPUs will be discussed. It may be noted that memory may be a relatively scarce resource on a GPU, and that transfers between the GPUs on-board memory and the host computer's memory (or memory of central processor) may be relatively expensive. For reasonably-sized problems, some data may be transferred between a host (e.g., central processing unit 110) and a distributed processing unit such as a GPU. The selection of what particular data remains on the GPU may be determined based on the given application, along with what data may be transferred between the GPU and the host, and how to hide the latency of these transfers (for example by simultaneously performing computations on the GPU. Various conventional approaches may be unacceptably slow due to data transfer delays, whereas the improved processing efficiency provided by various embodiments discussed herein provides for more practical implementation of MBIR, for example.

In various embodiments, an example algorithm (e.g., as described above) may be implemented by storing two image-sized vectors on a GPU. Namely, a vector g reflecting the current value of $x^{(n+1)}$ if the inner iterations were terminated (e.g., $g = x^{(n)} + d^{(n)}(u,v) = x^{(n)} - (1/\epsilon)(A^T u + C^T v)$), and a vector to store $v_d$ when updating a group of the regularizer dual variables. The latency of transferring $v_d$ to and from the GPU may be hidden by performing tomography updates between starting the transfer of $v_d$ to the GPU, updating $v_d$, and transferring $v_d$ back to the host.

Figure 3:
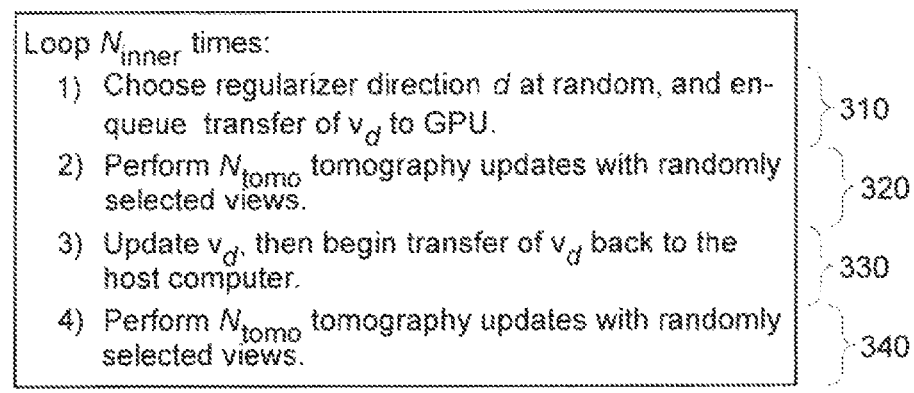
FIG. 3 illustrates an example process flow in accordance with various embodiments.

FIG. 3 illustrates an example process flow for implementation of an algorithm inner loop that hides the cost of transferring $v_d$ by interleaving transfers with tomography updates. As seen in FIG. 3, at 310, a regularizer direction is chosen at random, and a transfer process of $v_d$ to a GPU (e.g., first distributed processing unit 220) begins. At 320, $N_{tomo}$ tomography updates are performed with randomly selected views. At 330, $v_d$ is updated, and transfer of $v_d$ back to the host (e.g., central processing unit 210) is begun. At 340, $N_{tomo}$ tomography updates are performed with randomly selected views.

After $N_{inner}$ iterations, $x^{(n)}$ may be updated. One simple way of accomplishing this is to simply set the buffers storing v and u to zero. This restarts the update search problem (e.g., Eq. 4) from d=0, and the GPU vector g is equal to $x^{(n+1)}$. However, in various embodiments it may be useful to "warm-start" the next update search with the current values of $u^{(n)}$ and $v^{(n)}$. Consequently, g may be updated as follows:

$$g \leftarrow x^{(n+1)} - \frac{1}{\epsilon}(A^T u^{(n)}) = g + (g - x^{(n)})$$

Eq. 22

Figure 9:
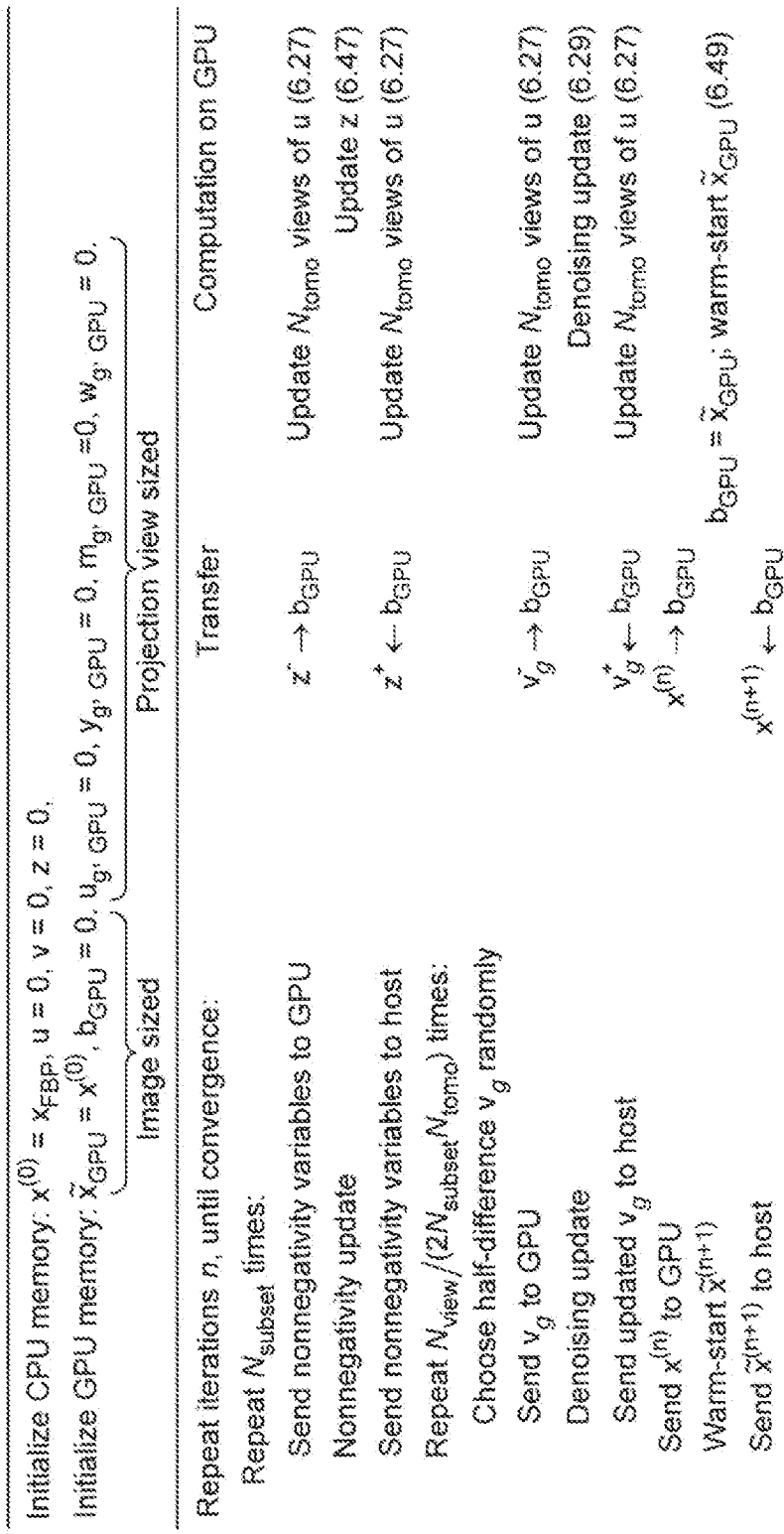
FIG. 9 provides pseudocode for an example algorithm alternating between sinogram and image domain information updates in accordance with various embodiments.

Accordingly, in various embodiments, updates based on sinogram information may be performed separately (e.g., alternately) with updates based on image domain data such as do-noising or non-negativity. FIG. 9 provides pseudocode for an example algorithm alternating between sinogram and image domain information updates in accordance with various embodiments.

As indicated herein, in various embodiments, the central processing unit 210 may be configured to distribute at least one of the sinogram information or the image domain information using block-separable surrogate functions. For example, the first distributed processing unit 220 may perform multiple iterations of a first block-separable surrogate function while the second distributed processing unit 230 performs multiple iterations of a second block-separable surrogate function.

Figure 4:
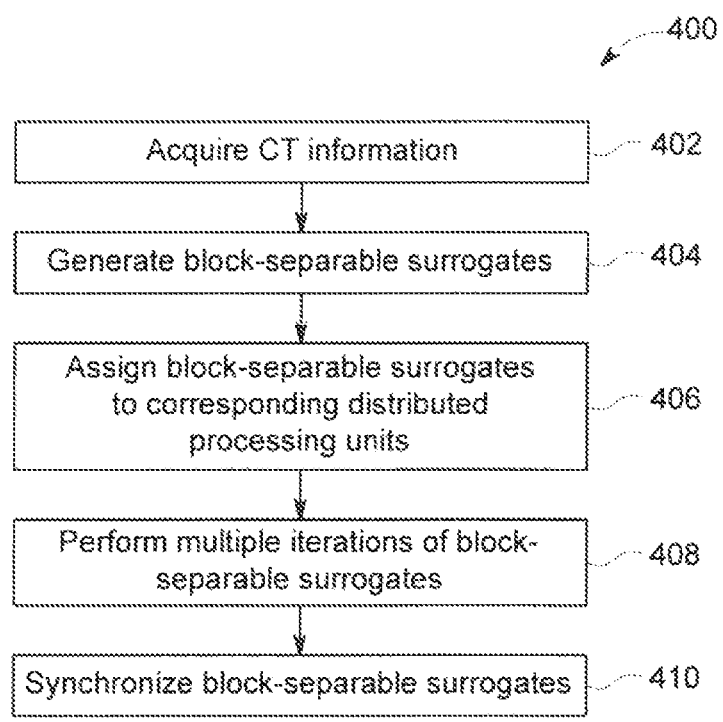
FIG. 4 is a flowchart of a method in accordance with various embodiments.

FIG. 4 provides a flowchart of a method 400 for performing block separable surrogate functions in accordance with various embodiments. The method 400, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be able to be used as one or more algorithms to direct hardware (e.g., one or more aspects of the processing unit 200 and/or image reconstructor 950) to perform one or more operations described herein.

At 402, CT information is acquired. The CT information may be collected by rotating an X-ray source and detector relative to an object to be imaged. In some embodiments, the CT information may also be collected by translating the X-ray source and detector axially or longitudinally relative to the object to be imaged. The axial or longitudinal translation may occur at the same time as the rotation in some embodiments (e.g., during a helical mode of operation), or may occur in steps or increments between rotations (e.g., during a step and shoot mode of operation). It may be noted that in some embodiments, the CT imaging information may be acquired from a storage device, memory device, and/or network or internet connection. The processors that acquire the CT imaging information for use in reconstruction may be integral with an acquisition unit as part of an imaging system located at a single location, or the processors may be located remotely from the acquisition unit.

At 404, block separable surrogate functions are generated. For example, sinogram or tomography information (e.g., as represented herein by L(x)) may be analyzed using block separable surrogate functions as discussed herein. The block separable functions may have an iterative form. Alternatively or additionally, image domain information (e.g., regularizer information) may be analyzed using block separable surrogate functions.

At 406, the block separable surrogate functions generated at 404 are assigned to corresponding distributed processors (e.g., first distributed processing unit 220, second distributed processing unit 230, third distributed processing unit 240). For example, each block separable surrogate component may be assigned to a particular separate or dedicated distributed processing unit which may optimize the assigned block separable surrogate component. In various embodiments, the distributed processors may be graphics processing units (GPU's) arranged in a parallel orientation with respect to a central processing unit.

At 408, multiple iterations of the block separable surrogates are independently performed using the corresponding distributed processors. For example, each of the distributed processor may perform a number of iterations of its assigned block separable surrogate component without using any additional information from any others of the processors during performance of the multiple iterations.

At 410, the block separable surrogates are synchronized. For example, after performing a number of iterations of the corresponding block separable surrogate components, the distributed processor may transfer information therebetween to update the block separable surrogate for each distributed processor using information from at least one other distributed processor.

Certain general considerations as well as particular examples of aspects of iterative reconstructive processes that may be used in conjunction with one or more aspects of the method 400 will now be discussed. Generally, statistical reconstruction for low-dose CT may provide desirable image quality, but the computation burden may be challenging, particularly for large 3D helical scans. Parallel computing may help reduce computation times, but simple parallelization methods for CT reconstruction may be hampered by relatively large data communication times between nodes that do not share memory. Various embodiments discussed herein relate to block-separable surrogate approaches to developing algorithms that facilitate parallelization. Various embodiments reduce communication between nodes and allow multiple independent updates on each node, while attempting to maintain convergence rates of recent accelerated algorithms.

Statistical X-ray CT reconstruction may reduce noise and artifacts using safer low-dose CT scans compared to conventional filtered back-projection (FBP) methods; however, statistical reconstruction (e.g., of large helical CT scan data) may require relatively long computation times. Previously, ordered subsets (OS) methods based on separable quadratic surrogates (SQS) have been used in CT research because they are parallelizable and heuristically reduce the computation cost by using only a subset of data per iteration. However, these efficient OS method are still slower than desired.

Distributed computing resources may be used to accelerate big data computational problems. For example, although a distributed implementation of OS-SQS method with momentum (OS-SQS-mom) has been utilized to reduce run time, data communication between nodes may become a bottleneck for such an approach, for example when using many nodes.

Various embodiments discussed herein reduce computation time further, while aiming to preserve a relatively fast convergence speed similar to a convergence speed of OS-SQS-mom. For example, a block-separable surrogate (BSS) technique may be adapted to CT scans (e.g., 3D helical CT scans). First, an OS-SQS-mom algorithm and distributed implementation thereof will be reviewed. Next, for example, to reduce communication time between nodes, BSS will be adapted with the OS-SQS-mom method.

First, an OS-SQS-mom algorithm is reviewed. For example, a patient image ($\hat{x} \in \mathbb{R}_+^{N_p}$) may be reconstructed by minimizing a penalized weighted least squares (PWLS) cost function (e.g., at strictly convex and continuously differentiable PWLS cost function):

$$\hat{x} = \underset{x \geq 0}{\operatorname{argmin}} \left\{ \psi(x) \triangleq L(x) + R(x) \right\} L(x) \triangleq \frac{1}{2} \|y - Ax\|_W^2 \quad \text{Eq. 23}$$

where $x \in \mathbb{R}_+^{N_p}$ is an (unknown) image, $y \in \mathbb{R}^{N_d}$ is noisy measured sinogram data, $A \in \mathbb{R}_+^{N_d \times N_p}$ is a forward projection operator, $W \in \mathbb{R}_+^{N_d \times N_d}$ is a diagonal statistical weighting matrix, and $R(x)$ is an edge-preserving regularizer.

Among many potential optimization methods, massively parallelizable SQS methods that iteratively minimize the SQS surrogate the nth iteration may be considered:

$$\psi(s) \leq \phi_{SQS}(x; x^{(n)}) \triangleq \psi(x^{(n)}) + \nabla \psi(x^{(n)})^T (x - x^{(n)}) + \frac{1}{2} \|x - x^{(n)}\|_D^2 \quad \text{Eq. 24}$$

for a diagonal majorizing matrix D, as $$x^{(n+1)} = \underset{x \geq 0}{\operatorname{argmin}} \phi_{SQS}(x; x^{(n)}) \quad \text{Eq. 25}$$

$$= [x^{(n)} \ldots D^{-1} \nabla \psi(x^{(n)})]_+ \quad \text{Eq. 26}$$

where $[\cdot]+$ enforces a non-negativity constraint. After computing the gradient, SQS updates each voxel independently. D may be chosen as:

$$D = \operatorname{diag}\{A^T W A 1\} + D^R \quad \text{Eq. 27:}$$

where $1 = \{1\} \in \mathbb{R}^{N_p}$ and $D^R$ is a majorizer for the Hessian of $R(x)$.

Computing the gradient in Eq. 26 may be expensive for large helical scans, so OS methods have been used with SQS by dividing $N_d$ projection data into (non-overlapping) M subsets and using the following approximation:

$$\nabla \psi(x) \approx M \nabla \psi_m(x) \quad \text{Eq. 28:}$$

$$\triangleq M A_m^T W_m (A_m x - y_m) + \nabla R(x) \quad \text{Eq. 29:}$$

For m=0, . . . , M-1, leading (empirically) to M-times acceleration in run time (for early iterations). The matrices $A_m$, $W_m$, and $y_m$ are submatrices of A, W, and y corresponding to the mth subset of $N_d$ projection data. It may be noted that the gradient of $R(x)$ may be small compared to the gradient of $L(x)$.

An OS-SQS-mom approach may be well-suited for parallelizable computing platforms that share memory, however, a typical implementation of OS-SQS-mom may be inefficient for distributed computing resources, for example because the computation of the gradient for $\psi_m(x)$ may require expensive global communications across nodes.

In previous distributed OS-SQS-mom approaches, because global communication for the gradient of $\psi_m(x)$ is expensive, the problem may be divided into S sub-problems (e.g., slabs of contiguous z-slices) with each sub-problem assigned to a cluster consisting of multiple nodes. However, because of the "long object" problem in helical CT, to reconstruct a slab of slices of interest, additional "padding" end slices may be required to be added. Such additional slices may reduce efficiency and limit how large S may be.

Mathematically, an image x may be divided into S (overlapping) sub-images $\{x_s\}$, with each problem solved separately:

$$\hat{x}_s = \underset{x_s \geq 0}{\operatorname{argmin}} \left\{ \breve{\psi}_{\sim s}(x_s) \triangleq \frac{1}{2} \|y - A_{\sim s} x_s\|_W^2 + \breve{R}_s(x_s) \right\}$$

for s=1, . . . , S, where $A_{\cdot,s} \in \mathbb{R}^{N_d \times |x_s|}$ is the system matrix and $R_s(x_s)$ is the regularizer for each s. The solutions $\{\hat{x}_s\}$ may differ from Eq. 23, particularly near the slab boundaries.

Even though slab positioning reduces communication, the communication within each cluster may remain a bottleneck. Accordingly, in various embodiments, a BSS technique may be adapted to reduce the global communications required for gradient computation.

For example, it may be desired for each node to perform multiple iterations before synchronizing, instead of communicating after every (subset) gradient. Also, it may be desirable for the algorithm to be guaranteed to converge in its one-subset (M=1) version. A BSS approach in various embodiments provide block-separable surrogates where each node may minimize its (non-overlapping) slab $x_b$ independently. In various embodiments, the BSS for B blocks (nodes) has the form:

$$\psi(x) \leq \phi_{BSS}(x; x^{(n)}) \triangleq \sum_{b=1}^{B} \left\{ \phi_{BSS,b}^L(x_b; x^{(n)}) + \phi_{BSS,b}^R(x_b; x^{(n)}) \right\} \quad \text{Eq. 30}$$

where the BSS surrogate of the quadratic $L(x)$ is defined as:

$$\phi_{BSS,b}^L(x_b; x^{(n)}) \triangleq C_b^{(n)} + (\nabla_b L(x^{(n)}))^T x_b - x_b^{(n)} + \frac{1}{2} \|x_b - x_b^{(n)}\|_{H_b^L}^2 \quad \text{Eq. 31}$$

for b=1, . . . , B where $L(x)^{(n)} = \Sigma_{b=1}^B C_b^{(n)}$. In some embodiments, the majorizer Hessian may be defined as:

$$H_b^L \triangleq A_{,b}^L W \Lambda^b A_{,b} \quad \text{Eq. 32:}$$

where $A_{l,b}$ is the columns of the system matrix corresponding to the slices in the bth slab and $$\Lambda^b \triangleq \operatorname{diag}\{A1\} \operatorname{diag}^{-1}\{A_{,b} 1_b\} \quad \text{Eq. 33}$$

for b=1, . . . , B. It may be noted that, in various embodiments:

$$\nabla^2 \psi(x) \leq \nabla^2 \phi_{BSS}(x; x^{(n)}) << D \quad \text{Eq. 34}$$

In various embodiments, an algorithm may be selected for minimizing the BSS majorizer (Eq. 30). In some embodiments, OS-SQS²-mom may be utilized, although it may be noted that other techniques may be employed in different embodiments.

Next, an example algorithm that iteratively minimizes the BSS surrogate function node-independently using OS-SQS-mom is considered. FIG. 5 summarizes an example distributed BSS algorithm that guarantees monotonic descent update and convergence for the one-subset (M=1) version. One difference between the example depicted in FIG. 5 and certain previous approaches is that the example depicted in FIG. 5 does not require communication when computing the gradient and image transfer after every update.

For the example of FIG. 5, it may be noted that the (mth subset) gradient may be computed efficiently as:

$$g_{m,b}^{(l)} = M A_{m,b}^T W_m \times \left\{ A_{m,b} z^{(0)} - y_m + \Lambda_m^b A_{m,b} \left( z_b^{\left(\frac{1}{M}\right)} - z_b^{(0)} \right) \right\} + \quad \text{Eq. 35}$$

-continued $$\nabla \phi_{BSS,b}^R(z_b^{(\frac{1}{M})}; z_b^{(0)})$$

requiring one (mth subset) forward and back projection. In the depicted embodiment, for example, a two-input forward projector may be employed that simultaneously computes $A_{m,b}z^{(0)}$ and $A_{m,b}(z_b^{(1/M)}-z_b^{(0)})$ with small overhead. For improved efficiency, in some embodiments, the matrix $\Lambda_b$ of Eq. 32 may be computed simultaneously with D of Eq. 27.

As indicated herein, in various embodiments, a distributed processing unit (e.g., first distributed processing unit 220) may utilize both resident information (or information previously generated by the first distributed processing unit 220) and non-resident information (e.g., information generated by other processing units) to perform a given operation. For example, with continued reference to FIG. 2, the first distributed processing unit 220 may begin performing an operation using the resident information while receiving non-resident information from one or both of the second distributed processing unit 230 and third distributed processing unit 240. The first distributed processing unit 220 may complete performing the operation using the non-resident information after the non-resident information has been received.

Figure 6:
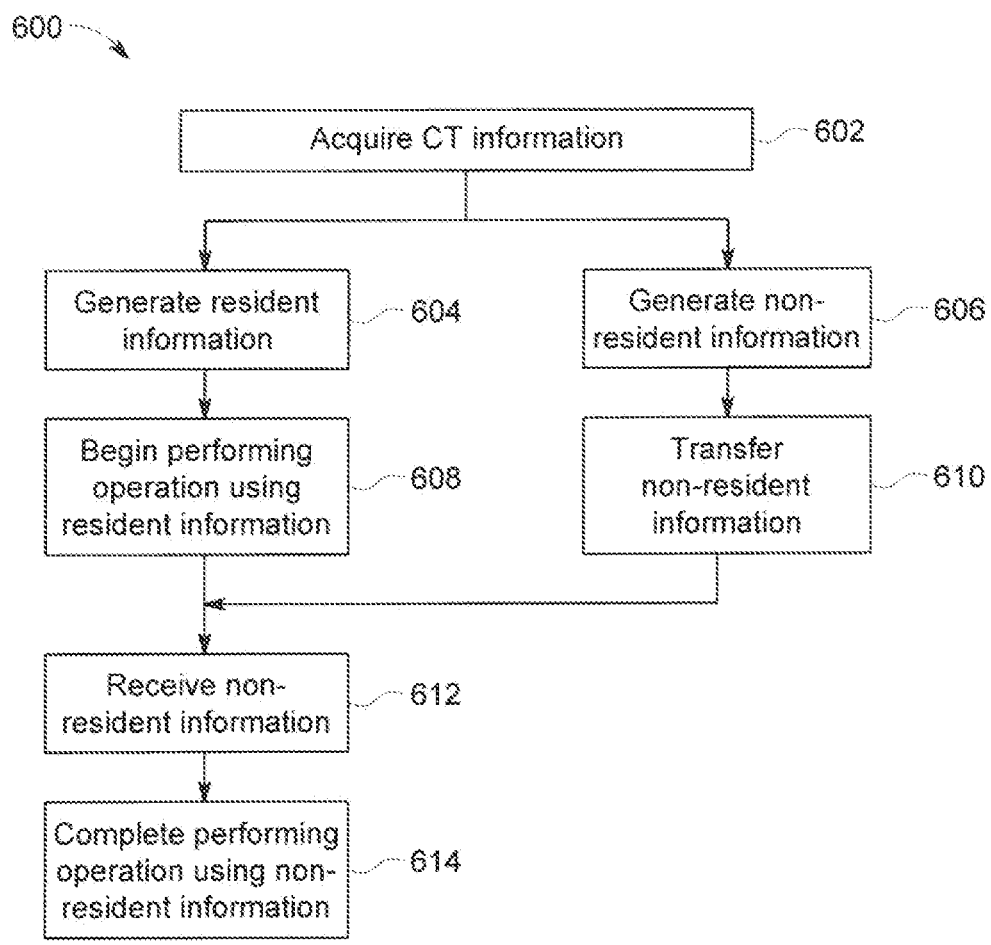
FIG. 6 is a flowchart of a method in accordance with various embodiments.

FIG. 6 provides a flowchart of a method 600 for performing just in time (JIT) data transfer or otherwise beginning performance of an operation using resident information while non-resident information is being transferred in accordance with various embodiments. The method 600, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 600 may be able to be used as one or more algorithms to direct hardware (e.g., one or more aspects of the processing unit 200 and/or image reconstructor 950) to perform one or more operations described herein.

At 602, CT information is acquired. The CT information may be collected by rotating an x-ray source and detector relative to an object to be imaged. In some embodiments, the CT information may also be collected by translating the x-ray source and detector axially or longitudinally relative to the object to be imaged. The axial or longitudinal translation may occur at the same time as the rotation in some embodiments (e.g., during a helical mode of operation), or may occur in steps or increments between rotations (e.g., during a step and shoot mode of operation). It may be noted that in some embodiments, the CT imaging information may be acquired from a storage device, memory device, and/or network or internet connection. The processors that acquire the CT imaging information for use in reconstruction may be integral with an acquisition unit as part of an imaging system located at a single location, or the processors may be located remotely from the acquisition unit.

At 604 resident information is generated. Resident information of a given processor may be understood as information generated by that processor, in contrast to information received by that processor from other processors. Accordingly, resident information of a given distributed processor is non-resident information of other distributed processors. The resident information may be generated, for example, by a back projection, by a forward projection, or by an image processing step. The resident information may be part of or utilized for a cost minimization solving operation and/or an updating operation used in connection with, for example, MBIR.

At 606, non-resident information is generated. Similar to resident information, non-resident information may be defined with respect to a particular distributed processor based on the origin of generation of the information. Non-resident information of a given processor may be understood as information generated by a different processor (e.g., information that must be transferred to the given processor), in contrast to information generated by that processor. As such, non-resident information of a given distributed processor is resident information of a different distributed processor. The non-resident information may be generated, for example, by a back projection, by a forward projection, or by an image processing step. The non-resident information may be part of or utilized for a cost minimization solving operation and/or an updating operation used in connection with, for example, MBIR.

At 608, performance of an operation (e.g., by a given distributed processor) is begun using resident information (e.g., of the particular distributed processor). The performance at 608 may be begun, for example, during at least a portion of a time of data transfer of non-resident information to be used for the same operation from one or more other distributed processors. The performance at 608 may be understood as using information resident on the particular distributed processor at an initial time, where the initial time may be understood as being at or shortly thereafter the completion of a previous operation or step by the particular distributed processor and before all of the information from a corresponding previous operation or step by one or more different distributed processors is transferred to the particular distributed processor. The operation begun at 608 may be, for example, a back projection, or, as another example, a forward projection.

At 610, non-resident information is transferred. In the illustrated embodiment, non-resident information from one or more additional distributed processors is transferred to the particular distributed processor that has begun performing the operation using resident information at 608. At 612, the non-resident information is received. Again, in the illustrated embodiment, the non-resident information is received by the particular distributed processor that has begun performing the operation using resident information at 608. It may be noted that, in various embodiments, the non-resident information may be received during at least a portion of a time already being utilized by the particular distributed processor to begin performing the operation using the resident information.

At 614, with the non-resident information received, performance of the operation is completed using the non-resident information now available. By beginning performance of the operation before all of the non-resident information was available, computational time is reduced and processing efficiency improved by the illustrated embodiment.

Figure 7:
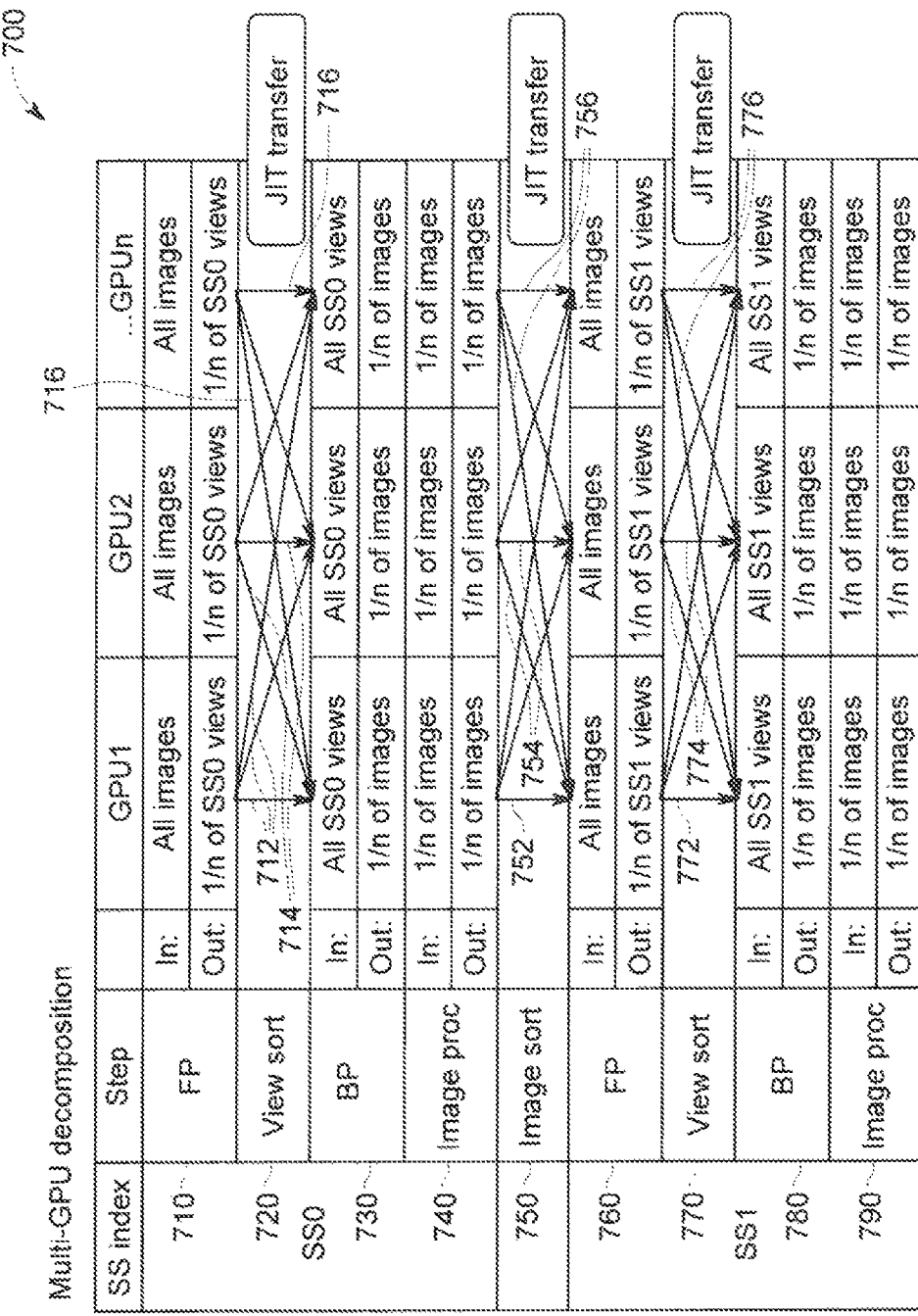
FIG. 7 depicts a process flow in accordance with various embodiments.

FIG. 7 depicts an example process flow 700. In the example process flow, certain operations are evenly divided among a number of distributed processors (GPU1, GPU2, . . . GPUn). It may be noted that in various embodiments, an image volume may be split in half (or otherwise) along a z-direction (or axial direction), and a sinogram may be split in half in a row direction, with the separated halves being computationally independent. Thus, for example, the GPU's shown in FIG. 7 may process half of an image volume while other GPU's process the other half.

As seen in FIG. 7, at 710 (a forward projection step) each of the depicted GPU's receives all images of an image volume to be processed as an input, and generates an output of 1/n of the resulting sinogram information generated by the forward projection. GPU1 generates output 712, GPU2 generates output 714, and GPUn generates output 716.

At 720, (a view sort step) information is transferred among the GPU's (e.g., via a central processing unit to which the depicted GPU's are connected in parallel). It may be noted that the output 712 is already resident on GPU1 and thus is available to GPU1 before the outputs 714 and 716 are available to GPU1. Accordingly, to save computational time, GPU1 may begin an operation using output 712 while outputs 714 and 716 are being transferred, and complete the operation once the outputs 714 and 716 are received.

For example, in the depicted embodiment, at 730 (a back projection step) GPU1 uses all of the sinogram information from step 720 as an input, and provides 1/n of the resulting images as an output, with GPU2 through GPUn providing the other (n–1)/n of the resulting images. To perform the back projection at 730, GPU1 eventually requires all of the sinogram information from steps 710 and 720; however, in the illustrated embodiment, GPU1 begins the back projection and performs the back projection to the extent possible using only the output 712 (the resident information). As the output 714 and 716 become available, GPU1 completes performance of the back projection. Similarly, GPU2 may begin its back projection using the output 714 (which is resident to GPU2), and GPUn may begin its back projection using the output 716 (which is resident to GPUn).

At 740 (an image processing step) each of the GPU's utilizes 1/n of the images from 730 (the 1/n resident thereon) as an input and provides an output of 1/n of the images.

At 750, (an image sort step) images are transferred among the GPU's (e.g., via a central processing unit to which the depicted GPU's are connected in parallel). It may be noted that the output 752 is already resident on GPU1 and thus is available to GPU1 before the outputs 754 and 756 are available to GPU1. Accordingly, to save computational time, GPU1 may begin an operation using output 752 while outputs 754 and 756 are being transferred, and complete the operation once the outputs 754 and 756 are received.

For example, in the depicted embodiment, at 760 (a second forward projection step), GPU1 uses all of the images from step 750 as an input, and provides 1/n of the resulting sinogram information as an output 772, with GPU2 through GPUn using all of the images from step 750 as an input, and providing the other (n–1)/n of the resulting sinogram information (as output 774 and 776, respectively). To perform the forward projection at 760, GPU1 eventually requires all of the images from steps 740 and 750; however, in the illustrated embodiment, GPU1 begins the forward projection and performs the forward projection to the extent possible using only the output 752 (the resident information). As the output 754 and 756 become available, GPU1 completes performance of the forward projection. Similarly, GPU2 may begin its forward projection using the output 754 (which is resident to GPU2), and GPUn may begin its forward projection using the output 756 (which is resident to GPUn).

Next, at 770, (a second view sort step) information is again transferred among the GPU's (e.g., via a central processing unit to which the depicted GPU's are connected in parallel). With output 772 is already resident on GPU1, output 772 is available to GPU1 before the outputs 774 and 776 are available to GPU1. Accordingly, to save computational time, GPU1 may begin an operation using output 772 while outputs 774 and 776 are being transferred, and complete the operation once the outputs 774 and 776 are received.

For example, in the depicted embodiment, at 780 (a second back projection step), GPU1 uses all of the sinogram information from step 770 as an input, and provides 1/n of the resulting images as an output, with GPU2 through GPUn providing the other (n–1)/n of the resulting images. To perform the back projection at 780, GPU1 eventually requires all of the sinogram information from steps 760 and 770; however, in the illustrated embodiment, GPU1 begins the back projection and performs the back projection to the extent possible using only the output 772 (the resident information). As the output 774 and 776 become available, GPU1 completes performance of the back projection. Similarly, GPU2 may begin its back projection using the output 774 (which is resident to GPU2), and GPUn may begin its back projection using the output 776 (which is resident to GPUn).

At 790 (a second image processing step) each of the GPU's again utilizes 1/n of the images from 780 (the 1/n resident thereon) as an input and provides an output of i/n of the images following an image processing operation.

Figure 8:
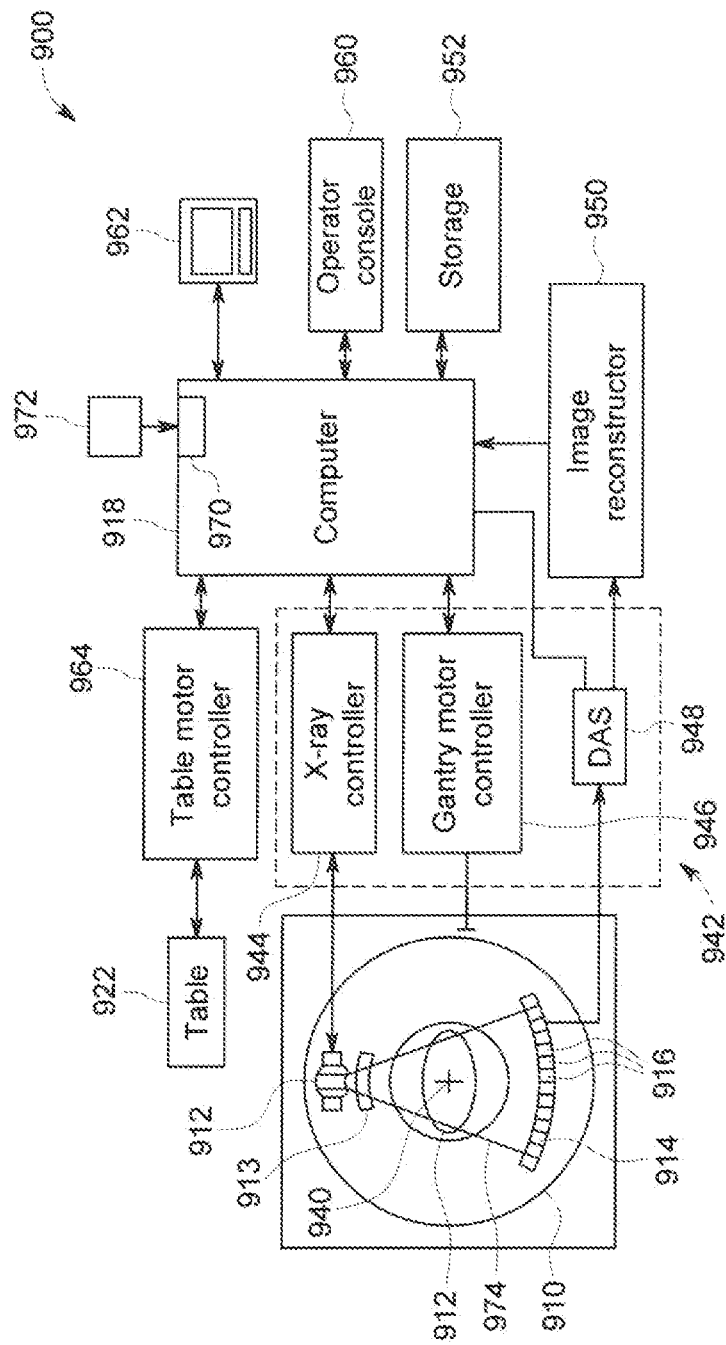
FIG. 8 is a schematic block diagram of an imaging system in accordance with various embodiments.

Various methods and/or systems (and/or aspects thereof) described herein may be implemented using a medical imaging system. For example, FIG. 8 is a block schematic diagram of an exemplary CT imaging system 900 that may be utilized to implement various embodiments discussed herein. Although the CT imaging system 900 is illustrated as a standalone imaging system, it should be noted that the CT imaging system 900 may form part of a multi-modality imaging system in some embodiments. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter are provided proximate the X-ray source 912. In various embodiments, the source collimator 913 may be configured to provide wide collimation as discussed herein. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

The depicted detector array 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 8 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 120 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view" or "projection." A "scan" of the subject 917 comprises a set of views made at different gantry angles, or view angles, during one or more revolutions of the X-ray source 912 and the detector array 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system substantially less than a full rotation may be utilized. Thus, in some embodiments, a scan (or slab) corresponding to a 360 degree view may be obtained using less than a complete revolution.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method for iteratively reconstructing an image, the method comprising:
   acquiring, with a detector, computed tomography (CT) imaging information;
   generating, with at least one processor, sinogram information from the CT imaging information;
   generating, with the at least one processor, image domain information from the CT imaging information;
   updating the image using the sinogram information; and
   updating the image using the image domain information, wherein the updating the image using the sinogram information and updating the image using the image domain information are performed separately and alternately in an iterative fashion, wherein the image is updated separately and independently using the sinogram information and the image domain information.

2. The method of claim 1, wherein the image domain information comprises regularizer information, wherein the regularizer information corresponds to relationships to neighboring pixels of a detector used to acquire the CT information.

3. The method of claim 2, wherein the regularizer information comprises difference information between adjacent pixels.

4. The method of claim 1, further comprising:
   minimizing, with the at least one processor, a sinogram cost function using the sinogram information to produce optimized sinogram information;
   minimizing, with the at least one processor, an image domain cost function using the image domain information to produce optimized image domain information;
   wherein the minimizing the image domain cost function and minimizing the sinogram cost function are performed separately and alternately in an iterative fashion; and
   reconstructing, with the at least one processor, the image using the optimized sinogram information and the optimized image domain information.

5. The method of claim 4, wherein the minimizing of the sinogram cost function and the minimizing of the image domain cost function are performed using convex conjugates.

6. The method of claim 4, wherein the minimizing of the image domain cost information comprises at least one of generating de-noising updates or generating non-negativity updates.

7. The method of claim 4, wherein the at least one processor includes a central processor and plural distributed processors, wherein the distributed processors are configured to perform parallel processing under the direction of the central processor, wherein the minimizing the sinogram cost function is performed by at least one of the distributed processors and the minimizing the image domain cost function is performed by at least one other of the distributed processors.

8. The method of claim 7, wherein at least some of the sinogram information is transferred from the central processing unit to the at least one distributed processing unit while the at least one other of the distributed processors is performing the minimizing of the image domain cost function.

9. The method of claim 7, wherein at least some of the image domain information is transferred from the central processing unit to the at least one other of the distributed processors while the at least one of the distributed processors is performing the minimizing of the sinogram cost function.

10. The method of claim 1, wherein the at least one processor includes a central processor and plural distributed processors, wherein the distributed processors are configured to perform parallel processing under the direction of the central processor, wherein the distributed processors comprise a first distributed processor and a second distributed processor, wherein the first distributed processor begins performing an operation on at least one of the sinogram information or the image domain information using resident information while receiving non-resident information from at least the second distributed processor, and wherein the first distributed processor completes performing the operation after receiving the non-resident information.

11. The method of claim 1, wherein the at least one processor includes a central processor and plural distributed processors, wherein the distributed processors are configured to perform parallel processing under the direction of the central processor, wherein the distributed processors comprises a first distributed processor and a second distributed processor, wherein the central processor distributes at least one of the sinogram information or the image domain information using block-separable surrogate functions, wherein the first distributed processor performs multiple iterations of a first block-separable surrogate function and the second distributed processor performs multiple iterations of a second block-separable surrogate function.

12. The method of claim 1, wherein the updating the image using the sinogram information and the updating the image using the image domain information are performed on a series of views of the CT imaging information, with a sequence of views employed selected randomly.

13. A reconstruction system comprising:
a central processor; and
plural distributed processors, wherein the distributed processors are configured to perform parallel processing under the direction of the central processor, wherein the reconstruction system is configured to:
acquire CT imaging information;
determine block-separable surrogates for analyzing the CT imaging information, the block-separable surrogates having components;
assign each component of the block-separable surrogates to a corresponding distributed processor, the corresponding distributed processor configured to minimize the component;
perform multiple iterations of minimizations of the components of the block-separable surrogates independently using the corresponding distributed processors; and
synchronize the block-separable surrogates after performing the multiple iterations using the corresponding distributed processors.

14. The reconstruction system of claim 13, wherein the reconstruction system is further configured to generate tomography information and regularizer information, and to determine the block-separable surrogates for the tomography information.

15. The reconstruction system of claim 13, wherein the distributed processors are graphics processing units (GPU's).

16. The reconstruction system of claim 13, wherein the block-separable surrogates have the form:

$$\psi(x) \leq \emptyset_{BSS}(x;x^{(n)})$$
$$\triangleq \Sigma_{b=1}^{B} \{\emptyset_{BSS,b}^{L}(x_b;x^{(n)}) = \emptyset_{BSS,b}^{R}(x_b;x^{(n)})\}$$

where the block-separable surrogate of a quadratic L(x) is defined as:

$$\phi_{BSS,b}^{L}(x_b; x^{(n)}) \triangleq C_b^{(n)} + (\nabla_b L(x^{(n)}))^T x_b - x_b^{(n)} + \frac{1}{2}\|x_b - x_b^{(n)}\|_{H_b^L}^2.$$

17. A reconstruction system comprising:
a central processor; and
plural distributed processors, wherein the distributed processors are configured to perform parallel processing under the direction of the central processor, wherein the reconstruction system is configured to perform an operation utilizing resident information initially resident upon one of the distributed processors and non-resident information transferred from at least one other of the distributed processors, wherein the one of the distributed processors is configured to:
begin performing the operation using the resident information;
receive the non-resident information during at least a portion of a time utilized to begin performing the operation using the resident information; and
complete performing the operation using the non-resident information.

18. The reconstruction system of claim 17, wherein the one of the distributed processor is further configured to transfer the resident information of the one of the distributed processors to the at least one other of the distributed processors.

19. The reconstruction system of claim 17, wherein the resident information comprises sinogram information generated by a forward projection of imaging information.

20. The reconstruction system of claim 17, wherein the resident information comprises information generated by an image processing operation.

* * * * *